United States Patent [19]
Sarlikiotis et al.

[11] Patent Number: 5,527,539
[45] Date of Patent: Jun. 18, 1996

[54] TABLETS WITH THIOCTIC ACID OF SPECIFIC PARTICLE SIZE

[75] Inventors: Werner Sarlikiotis, Frankfurt; Helmut Hettche, Dietzenbach, both of Germany

[73] Assignee: ASTA Medica Aktiengesellschaft, Dresden, Germany

[21] Appl. No.: 367,480

[22] Filed: Jan. 5, 1995

[30] Foreign Application Priority Data

Jan. 10, 1994 [DE] Germany ............... 44 00 269.6

[51] Int. Cl.⁶ ................................... A61K 9/20
[52] U.S. Cl. ............. 424/464; 424/465; 514/951
[58] Field of Search ................... 424/464, 465; 514/951

[56] References Cited

U.S. PATENT DOCUMENTS

| 4,678,670 | 7/1987 | Tomic | 424/127 |
| 5,118,505 | 6/1992 | Költringer | 424/195.1 |
| 5,376,382 | 12/1994 | Goede et al. | 424/464 |

*Primary Examiner*—James M. Spear
*Attorney, Agent, or Firm*—Cushman Darby & Cushman

[57] ABSTRACT

The invention relates to a drug formulation in the form of tablets containing thioctic acid (α-lipoic acid) with an active ingredient content between 45% by weight and 99.9% by weight. The invention is characterized in that 20% to 100% of the active ingredient used has a particle size exceeding 100 μm, particulary between 100 μm and 710 μm, preferably 30% to 80% a particle size between 200 μm and 710 μm.

17 Claims, No Drawings

TABLETS WITH THIOCTIC ACID OF SPECIFIC PARTICLE SIZE

DESCRIPTION

The invention relates to a drug formulation in tablet form containing thioctic acid of specific particle size as well as pharmaceutically safe adjuvants if required.

In chemical terms thioctic acid (α-lipoic acid) is a 1,2-di-thiacyclopentane-3-valeric acid. The invention relates not only to the racemic form but also to the pure (R)-and/or (S)-thioctic acid and to mixtures of (R)- and (S)-thioctic acid of any composition. Thioctic acid is a constituent of cell metabolism and is therefore found in many plants and animal organisms. It acts as one of the coenzymes in the oxidative decarboxylation of pyruvate and other α-keto acids. For a long time now thioctic acid has been used in a number of diseases, including liver diseases, liver damage due to mushroom poisoning and in diabetic and alcoholic polyneuropathy, a change in peripheral nerves which accompanies metabolic diseases.

To facilitate taking and to increase acceptance by the patient, there is a need for more highly concentrated thioctic acid tablets with a smaller size.

With active ingredient dosages of more than 500 mg per tablet, the proportional multiplication of the constituents in the tablet containing 200 mg of thioctic acid already leads to tablets with individual weights exceeding 1.2 g. Because of their size tablets of such a high individual weight can only be swallowed with difficulty, which causes their acceptance to diminish. It is required to reduce the proportion of adjuvant in the higher-dosage solid forms of the drug. Tablets containing thioctic acid and with a reduced adjuvant content cannot, however, be produced to a satisfactory quality with customary manufacturing methods. Higher concentrations of thioctic acid lead to problems when compressing the tablets. The moulding compounds tend to adhere to the compression tools. Furthermore, cracks parallel to the surface occur in the tablets, and in the case of biconvex tablets the spherical caps (lids) burst off (capping). These problems are caused by the properties of the thioctic acid; the low melting point of the substance of 60.5° C. (R, S-thioctic acid) or 48.3° C. (R-thioctic acid) and 48.5° C. (S-thioctic acid) proves to be particularly critical.

By reducing the excipients content in the tablet, the probability of intolerance reactions such as to lactose is reduced at the same time (Deutsche Apothekerzeitung (German Pharmacists' Journal) 131, 1569 (1991)).

A possible solution to the problem which has already been described consists of granulating the active ingredient thioctic acid with a great deal of water (see EP 0 560 092 A1). The drawback to this procedure is that there is a risk of excessively wetting the granules so that subsequent drying can only be undertaken with difficulty, as a semi-liquid mixture can result. Furthermore, the drying of granulates with a high liquid content is generally complicated, cost-intensive and tiresome.

Surprisingly it has now been found that the compressibility of thioctic acid into tablets can be substantially improved by the use of thioctic acid of specific particle size. It is advantageous that 20% to 100% of the thioctic acid used has a particle size exceeding 100 μm, in particular that 30% to 80% of the active ingredient particles exceed 200 μm. Ideally 20% to 100% of the thioctic acid used should consist of particles between 100 μm and 710 μm and in particular 30% to 80% of particles between 200 μm and 710 μm. The use of fine-crystalline thioctic acid of which 90% has a grain size <50 μm produces unsatisfactory results when producing tablets.

As fine-grained thioctic acid tends to agglomerate, screening analysis is not suitable for determining the size distribution of these active ingredient particles. Laser diffraction spectrometry is more suitable for this. Both methods are, however, suitable for coarser active ingredient. The results obtained refer to distributions by volume and hence by mass.

Known methods are used to manufacture the tablets according to the invention. The active ingredient can be wetted with a liquid alone or as a mixture with adjuvants for example. If required the moist compound is then passed through a straining machine with a circular die ("Alexanderwerk-Reibschnitzler", Stephan granulating machine for example) for a granulating screen.

The further processing steps are carried out according to the prior art, viz. drying, screening if required, mixing with further adjuvants and compressing into tablets, for example.

The mixtures produced according to the method described can be compressed into tablets without problems, there is no adhesion to the compression tools.

Alcohols with 1–4 C atoms, esters of lower organic acids and lower organic alcohols with up to 6 C atoms in total, such as methanol, ethanol, isopropanol, ethyl acetate and particularly preferably water, can be used as liquids for granulation. Solutions of binders can also be used in granulation.

All pharmaceutically common binders such as cellulose derivatives (such as ethyl cellulose, methyl cellulose, hydroxyethyl cellulose, carboxymethyl cellulose, hydroxypropylmethyl cellulose), gelatins, starch, polyglycols (mean molecular mass 1000–35000 Dalton), polyvinyl alcohols, polyvinyl pyrrolidone, polyacrylic acid, vinylpyrrolidone-vinyl acetate copolymer, alginates, saccharose or glucose, polysaccharides, such as, for example, natural forms of gums such as gum arabic, gum tragacanth, pectin, guar gum in quantities of 1–30% by weight, preferably 5–20% by weight, particularly 10–15% by weight, related to the active ingredient can be used as binders for this purpose (concentration of the aqueous binder solutions 2–30% by weight, preferably 5–15% by weight).

Different binders, such as different cellulose derivatives alongside each other, can also be used at the same time. The binders can be incorporated into the dry powder mixture or be introduced into the granulation liquid dissolved or dispersed. The combination of dry and dissolved and/or dispersed binder is also suitable.

In addition to the thioctic acid the granulate can also contain common tablet adjuvants such as fillers, disintegrating agents and wetting agents. In addition to the granulate the tablet can also contain further fillers, binders, disintegrating agents, wetting agents, flow agents, lubricants and adhesion inhibitors. It is also possible to use the thioctic acid direct in non-granulated form.

If required, the granulate or the active ingredient is mixed with fillers, binders, suspending agents, wetting agents, flow agents, lubricants and/or adhesion inhibitors. Cellulose, cellulose derivatives, saccharose, lactose, glucose, fructose, calcium phosphates, calcium sulphates, calcium carbonates, starch, modified starch, sugar alcohols such as sorbitol or mannitol are examples of fillers that can be used.

The binders already quoted above are suitable as binders. Starch, modified starch (such as sodium starch glycolate, Starch 1500), cellulose, cellulose derivatives, alginates, crosslinked polyvinyl pyrrolidone or crosslinked carboxymethyl cellulose (Ac—Di—Sol/FMC) can be used as disintegrating agents, for example.

Sodium dioctylsulphosuccinate, sodium lauryl sulphate, polysorbates or polyoxyethylene stearic acid esters can be used as wetting agents for example. Examples of suitable flow agents are colloidal silicon dioxide, talcum or magnesium stearate.

Examples of lubricants which can be used are magnesium stearate, calcium stearate, D.L-leucine, talcum, stearic acid, polyglycols (mean molecular mass 3000–35000), fatty alcohols or waxes. Examples of adhesion inhibitors which can be used are starch, talcum, magnesium stearate, calcium stearate or D.L-leucine.

The mixture produced in this way is compressed into tablets in the usual way. It can be advantageous to reduce the temperature of the mixture below room temperature prior to compression. The temperature can be 0° C.–30° C., preferably 5° C.–20° C., particularly 8° C.–15° C.

The drug formulations according to the invention contain between 45% by weight and 99.9% by weight of active ingredient, preferably between 55% by weight and 99.9% by weight, particularly between 73% by weight and 99.9% by weight and particularly preferably between 80% by weight and 99.9% by weight of active ingredient.

The tablets can be provided with a gastric juice-permeable or -soluble coating according to customary methods.

EXAMPLE 1

Tablets with 600 mg of Thioctic Acid to 684 mg Tablet weight (Granulation method)

200 g of thioctic acid, 60% having a particle size >100 μm, are mixed with 120 g of hydroxypropyl cellulose, low substituted (L-HPC-LH 22/Shin Etsu) and the mixture wetted with 600 g of purified water and mixed up. After passing through a screen of 2 mm sieve opening the granulate is dried, again screened through a screen of 1 mm sieve opening and, after the addition of 48 g of magnesium stearate, compressed into tablets of oblong format with a weight of 684 mg, a length of 18 mm, a width of 8 mm and a radius of curvature of 6 mm. A tablet contains 600 mg of thioctic acid. Tabletting presents no problems. The tablets can then be provided with a gastric juice-permeable or gastric juice-soluble film coating according to customary standard methods.

EXAMPLE 2

Tablets with 600 mg of Thioctic Acid to 684 mg Tablet Weight (Granulation method)

The following example is intended to illustrate the problems which arise when fine-grained active ingredient is used. The composition and the method of manufacture are identical to Example 1.

1200 g of thioctic acid, 90% having a particle size <50 μm, are mixed with 120 g of hydroxypropyl cellulose, low substituted (L-HPC-LH 22/Shin Etsu) and the mixture wetted with 600 g of purified water and mixed up. After passing through a screen of 2 mm sieve opening the granulate is dried, again screened through a screen of 1 mm sieve opening and, after the addition of 48 g of magnesium stearate, compressed into tablets of oblong format with a weight of 684 mg, a length of 18 mm, a width of 8 mm and a radius of curvature of 6 mm. A tablet contains 600 mg of thioctic acid. After a short time, extensive adhesion of the granulated mass to the tabletting punches takes place. As this effect cannot be remedied by changing the settings of the tablet pressing machine the compression process has to be stopped.

EXAMPLE 3

Tablets with 200 mg of Thioctic Acid to 235 mg Tablet Weight (Direct moulding compound)

2100.00 g of thioctic acid according to the invention are mixed with 113.75 g of lactose, 175.00 g of microcrystalline cellulose, 17.5 g of polyvidone, 29.75 g of corn starch and 1.75 g of highly dispersed silicondioxide. 29.75 g of magnesium stearate are then added to this mixture which is then mixed again. The moulding compound produced in this way is compressed into tablets with a weight of 235 mg. The tablets contain 200 mg of thioctic acid, which corresponds to an active ingredient content of 85.1%.

We claim:

1. Drug formulation in the form of compressed tablets containing thioctic acid (α-lipoic acid) with a content between 45% by weight and 99.9% by weight, characterized in that 20% to 100% of the active ingredient used has a particle size exceeding 100 μm.

2. Drug formulation in the form of compressed tablets containing thioctic acid (α-lipoic acid) with a content between 55% by weight and 99.9% by weight, characterized in that 20% to 100% of the active ingredient used has a particle size exceeding 100 μm.

3. Drug formulation in the form of compressed tablets containing thioctic acid (α-lipoic acid) with a content between 73% by weight and 99.9% by weight, characterized in that 20% to 100% of the active ingredient used has a particle size exceeding 100 μm.

4. Drug formulation in the form of compressed tablets containing thioctic acid (α-lipoic acid) with a content between 80% by weight and 99.9% by weight, characterized in that 20% to 100% of the active ingredient used has a particle size exceeding 100 μm.

5. Drug formulation in the form of compressed tablets containing thioctic acid (α-lipoic acid) with a content between 45% by weight and 99.9% by weight, characterized in that 20% to 100% of the active ingredient used has a particle size of 100 μm to 710 μm.

6. Drug formulation in the form of compressed tablets containing thioctic acid (α-lipoic acid) with a content between 55% by weight and 99.9% by weight, characterized in that 20% to 100% of the active ingredient used has a particle size of 100 μm to 710 μm.

7. Drug formulation in the form of compressed tablets containing thioctic acid (α-lipoic acid) with a content between 73% by weight and 99.9% by weight, characterized in that 20% to 100% of the active ingredient used has a particle size of 100 μm to 710 μm.

8. Drug formulation in the form of compressed tablets containing thioctic acid (α-lipoic acid) with a content between 80% by weight and 99.9% by weight, characterized in that 20% to 100% of the active ingredient used has a particle size of 100 μm to 710 μm.

9. Drug formulation in the form of compressed tablets containing thioctic acid (α-lipoic acid) with a content between 45% by weight and 99.9% by weight, characterized in that 30% to 80% of the active ingredient used has a particle size exceeding 200 μm.

10. Drug formulation in the form of compressed tablets containing thioctic acid (α-lipoic acid) with a content between 55% by weight and 99.9% by weight, characterized in that 30% to 80% of the active ingredient used has a particle size exceeding 200 μm.

11. Drug formulation in the form of compressed tablets containing thioctic acid (α-lipoic acid) with a content between 73% by weight and 99.9% by weight, characterized in that 30% to 80% of the active ingredient used has a particle size exceeding 200 μm.

12. Drug formulation in the form of compressed tablets containing thioctic acid (α-lipoic acid) with a content between 80% by weight and 99.9% by weight, characterized in that 30% to 80% of the active ingredient used has a particle size exceeding 200 μm.

13. Drug formulation in the form of compressed tablets containing thioctic acid (α-lipoic acid) with a content between 45% by weight and 99.9% by weight, characterized in that 30% to 80% of the active ingredient used has a particle size of 200 μm to 710 μm.

14. Drug formulation in the form of compressed tablets containing thioctic acid (α-lipoic acid) with a content between 55% by weight and 99.9% by weight, characterized in that 30% to 80% of the active ingredient used has a particle size of 200 μm to 710 μm.

15. Drug formulation in the form of compressed tablets containing thioctic acid (α-lipoic acid) with a content between 73% by weight and 99.9% by weight, characterized in that 30% to 80% of the active ingredient used has a particle size of 200 μm to 710 μm.

16. Drug formulation in the form of compressed tablets containing thioctic acid (α-lipoic acid) with a content between 80% by weight and 99.9% by weight, characterized in that 30% to 80% of the active ingredient used has a particle size of 200 μm to 710 μm.

17. Drug formulation according to one of claims 1 to 16, characterized in that in addition to thioctic acid, further physiologically acceptable excipients are contained in said compressed tablets.

* * * * *